United States Patent [19]

Neumann et al.

[11] Patent Number: 4,982,005
[45] Date of Patent: Jan. 1, 1991

[54] PREPARATION OF BENZOPHENONES

[75] Inventors: Peter Neumann, Mannheim; Ulrich Eichenauer, Frankfurt, both of Fed. Rep. of Germany

[73] Assignee: BASF Aktiengesellschaft, Ludwigshafen, Fed. Rep. of Germany

[21] Appl. No.: 397,873

[22] Filed: Aug. 23, 1989

[30] Foreign Application Priority Data

Sep. 13, 1988 [DE] Fed. Rep. of Germany ....... 3831092

[51] Int. Cl.$^5$ .............................................. C07C 45/46
[52] U.S. Cl. ..................................... 568/319; 568/42; 568/63
[58] Field of Search ..................... 568/319, 322, 42, 63

[56] References Cited

U.S. PATENT DOCUMENTS 4,777,300  10/1988  Colquhoun et al. ................ 568/319

FOREIGN PATENT DOCUMENTS 10057503  1/1982  European Pat. Off. .
10069598  7/1982  European Pat. Off. .
202403   11/1986  European Pat. Off. ............ 568/319
643433    3/1971  Fed. Rep. of Germany ...... 568/319
375033    9/1964  France .
1375033   9/1964  France .
190943    9/1984  Japan .
61-97240  5/1986  Japan ................................... 568/319
2102420   2/1983  United Kingdom .

OTHER PUBLICATIONS

Steinbach et al., Chem. Abst., vol. 106, #49811m (1987).
Chem. Ber., vol. 66, 1933, pp. 411–414.
Chem. Ber., vol. 87, 1954, pp. 194–202.
Archiv Pharm., vol. 287, 1954, pp. 210–223.
*Chemische Berichte,* 87. Jahrgang, 1954, Verlag Chemie Weinheim/Bergstrasse Karl Kindler et al., "Studien ueber den Mechanismus chemischer . . . ".
Die Pharmazie, vol. 9, 1954, pp. 98–113.

*Primary Examiner*—James H. Reamer
*Attorney, Agent, or Firm*—Oblon, Spivak, McClelland, Maier & Neustadt

[57] ABSTRACT

Benzophenones are prepared by condensing benzoic acids and aromatics of the benzene series by means of boron trifluoride in nitrobenzene as reaction medium.

13 Claims, No Drawings

PREPARATION OF BENZOPHENONES

THE INVENTION

1. Field of the Invention:

The present invention relates to a novel process for preparing benzophenones by reacting benzoic acids and aromatics of the benzene series in the presence of boron trifluoride in nitrobenzene as the reaction medium.

2. Discussion of the Background

The use of boron trifluoride as activating reagent for the condensation of carboxylic acids with reactive aromatics to give aromatic ketones is known and described for example in Chem. Ber. 66 (1933), 411; Chem. Ber. 87 (1954), 194; Arch. Pharm. 287 (1954), 210; and Pharmazie 1954, 102. It is customary in this reaction to use the carboxylic acid as solvent, although in some instances the other reactant is used. This is uneconomical in the case of valuable reactants and, what is more, requires that in the case of solid reactants the reaction be carried out in a melt, which is technically very complicated.

To avoid these disadvantages, the use of diluents has been proposed. For instance, FR-A-1,375,033 proposes the preparation of benzophenones by reacting boron trifluoride complexes of the reactants in trichloroethylene as diluent. But the particular boron trifluoride complexes required must be prepared in a separate stage. Also, trichloroethylene is toxicologically suspect.

JP-A-190,943/1984 describes the use of chlorobenzene as a reaction medium. In this case, however, low solubility of the boron trifluoride complexes of the reactants in this medium is a disadvantage, leading to prolonged reaction times and poor yields.

SUMMARY OF THE INVENTION

It is an object of the present invention to provide a novel process for preparing benzophenones which likewise uses boron trifluoride as catalyst but avoids the abovementioned disadvantages.

We have found that this object is achieved by preparing a benzophenone of the formula I

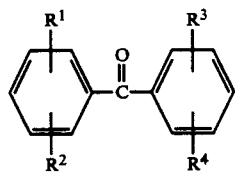

where
R$^1$ and R$^2$ are identical or different and each is independently of the other hydrogen, C$_1$–C$_4$-alkyl, substituted or unsubstituted phenyl, halogen, hydroxyl, mercapto, C$_1$–C$_4$-alkoxy, substituted or unsubstituted phenoxy, C$_1$–C$_4$-alkylthio or substituted or unsubstituted phenylthio and
R$^3$ and R$^4$ are identical or different and each is independently of the other hydrogen, hydroxyl, C$_1$–C$_4$-alkoxy, substituted or unsubstituted phenoxy, C$_1$–C$_4$-alkylthio or substituted or unsubstituted phenylthio,
by reacting a benzoic acid of the formula II

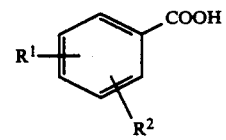

where R$^1$ and R$^2$ are each as defined above, with an aromatic from the benzene series which conforms to formula III

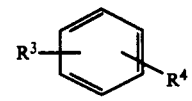

where R$^3$ and R$^4$ are each as defined above, in the presence of boron trifluoride as a catalyst in nitrobenzene as reaction medium.

DETAILED DESCRIPTION OF THE PREFERRED EMBODIMENT

All the alkyl groups appearing in the abovementioned formula I can be not only straight-chain but also branched.

If substituted phenyl appears in the above-mentioned formula I, suitable substituents are for example C$_1$–C$_4$-alkyl, C$_1$–C$_4$-alkoxy, hydroxyl, halogen and carboxyl.

R$^1$, R$^2$, R$^3$ and R$^4$ are each for example methoxy, ethoxy, propoxy, isopropoxy, butoxy, isobutoxy, sec-butoxy or tert-butoxy.

R$^1$ and R$^2$ are each further for example methyl, ethyl, propyl, isopropyl, butyl, isobutyl, sec-butyl, tert-butyl, phenyl, 2- or 4-hydroxyphenyl, 2-methylphenyl, fluorine, chlorine, bromine, 4-carboxyphenoxy, 4-chlorophenoxy, methylthio, ethylthio, propylthio, isopropylthio, butylthio or 4-methylphenylthio.

Suitable benzoic acids of the formula II are for example benzoic acid, 2-hydroxybenzoic acid, 3-hydroxybenzoic acid, 4-hydroxybenzoic acid, 2,4-dihydroxybenzoic acid, 3,5-dihydroxybenzoic acid, 2-methoxybenzoic acid, 3-methoxybenzoic acid, 4-methoxybenzoic acid, 2-fluorobenzoic acid, 3-fluorobenzoic acid, 4-fluorobenzoic acid, 2-chlorobenzoic acid, 3-chlorobenzoic acid, 4-chlorobenzoic acid, 2-bromobenzoic acid, 3-bromobenzoic acid, 4-bromobenzoic acid, 2-methylbenzoic acid, 3-methylbenzoic acid, 4-methylbenzoic acid, 2-phenylbenzoic acid, 3-phenylbenzoic acid, 4-phenylbenzoic acid, 4-hydroxybiphenyl-4'-carboxylic acid, 2,4-dimethoxybenzoic acid, 2,6-dimethoxybenzoic acid, 4-carboxydiphenyl ether and 4,4'-dicarboxydiphenyl ether.

Suitable aromatics of the formula III are for example benzene, phenol, phloroglucine, resorcinol, hydroquinone, anisole, resorcinol dimethyl ether, hydroquinone dimethyl ether and hydroquinone methyl ether.

The process according to the invention is advantageously carried out by initially introducing the benzoic acid of formula II and the aromatic of the benzene series (formula III) in nitrobenzene and injecting boron trifluoride gas into this mixture, customarily at room temperature, with stirring This is followed by the condensation reaction, which is carried out with stirring at from 20° to 200° C., preferably at from 20 to 130° C, in particular from 50° to 90° C. The reaction will in general have ended within from 0.5 to 5 hours.

To work up the reaction mixture, it may be subjected for example to a steam distillation in order to remove the nitrobenzene, in which case the benzophenone of the formula I generally crystallizes out of the remaining aqueous mother liquor on cooling. The nitrobenzene removed by means of steam may be recycled into the reaction after regeneration.

A preferred workup procedure comprises extracting the reaction mixture with water in a liquid-liquid extractor at an elevated temperature under either atmospheric or superatmospheric pressure. The extraction temperature is in general at from 80° C. to the boiling point of water under the pressure employed, preferably at from 90° to 100° C. The pressure at which the extraction is carried out can be set at from 0.9 to 10 bar, atmospheric pressure being preferred. The amount of water used for the extraction can be from 50 to 1000% by weight, based on the nitrobenzene used. The extraction can be carried out batchwise or, preferably, continuously. Particular preference is given to a continuous procedure where the water is evaporated from the aqueous extract and then reused for the extraction.

To isolate the target product, the aqueous extract is cooled and filtered. It may also be possible to isolate the useful product from the cooled organic phase by filtration The filtration of the aqueous phase can be carried out continuously or batchwise independently of the extraction.

Compared with steam distillation, an extractive workup gives still better yields and a target product of still better color quality. A further advantage is that less water is contaminated with nitrobenzene. This is ecologically important.

In the process according to the invention, the boron fluoride is in general used in a ratio of from 1 to 3 moles per mole of benzoic acid II.

The molar ratio of benzoic acid II: aromatic III is in general from 1:0.5 to 1:2.

Owing to the excellent solubility of the boron trifluoride complexes of the reactants, the amount of nitrobenzene used as reaction medium can be kept to a minimum. It is customarily from 100 to 250% by weight, based on the total weight of benzoic acid II and aromatic III.

The novel process is also notable for a short reaction time and a low reaction temperature. The target products are in general obtained in high purity and therefore can be reused without further purification.

The benzophenones prepared by means of the process according to the invention, which may be carried out continuously or batchwise, are suitable for use as UV absorbers or as monomers for high temperature resistant polymers.

The following Examples will explain the invention in more detail:

EXAMPLE 1

27.5 g of resorcinol and 30.5 g of benzoic acid were suspended in 100 ml of nitrobenzene. 34 g of boron trifluoride gas were then passed into this suspension. The reaction mixture was heated to 80° C. and maintained at that temperature for 30 minutes. After cooling down, the mixture was steam distilled. The target product, 2,4-dihydroxybenzophenone, crystallized out of the mother liquor on cooling. Yield: 51.2 g (96%); purity as per HPLC: 99.8%.

The benzophenones listed below in the Table were obtained in a similar manner.

TABLE

| Example No. | Benzoic acid II | Aromatic III | Benzophenone I | Yield [%] | Purity as per HPLC [%] |
|---|---|---|---|---|---|
| 2 | 2,4-Dihydroxybenzoic acid | Resorcinol | 2,2',4,4'-Tetrahydroxybenzophenone | 59 | 98.5 |
| 3 | 4-Hydroxybenzoic acid | Phenol | 4,4'-Dihydroxybenzophenone | 67 | 95 |
| 4 | 2-Hydroxybenzoic acid | Phenol | 2,4'-Dihydroxybenzophenone | 83 | 93 |
| 5 | 4-Hydroxybenzoic acid | Hydroquinone | 3,',4,5'-Trimethoxybenzophenone | 64 | |
| 6 | 4-Hydroxybenzoic acid | Anisole | 4-Hydroxy-4'-methoxybenzophenone | 74 | |
| 7 | Benzoic acid | 1-Hydroxy-3-methoxybenzene | 2-Hydroxy-4-methoxybenzophenone | 59 | |
| 8 | 4-Hydroxybiphenyl-4'-carboxylic acid | Phenol | 4-(4''-Hydroxyphenyl)-4'-hydroxybenzophenone | 84 | |

EXAMPLE 9

220 g of resorcinal and 308 g of 2,4-dihydroxybenzoic acid were suspended in 1 l of nitrobenzene, and 138 g of boron trifluoride were passed in at 24°–40° C. (slightly exothermic reaction). The reaction mixture was heated at 80° C. for 30 minutes and then introduced into a preheated continuous liquid-liquid extractor operated with 1.5 l of water at 98° C. Water was distillatively recycled from the extract and reused for the extraction. After 10 hours, the aqueous phase was separated off and cooled, and the crystallized product was filtered off under suction. Yield: 315 g (64%); purity as per HPLC: 99.6%.

We claim:
1. A process for preparing a benzophenone of the formula I

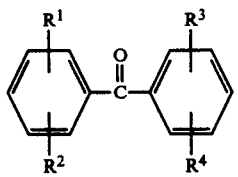

(I)

where

R¹ and R² are identical or different and each is independently of the other hydrogen, $C_1$–$C_4$-alkyl, substituted or unsubstituted phenyl, halogen, hydroxyl, mercapto, $C_1$–$C_4$-alkoxy, substituted or unsubstituted phenoxy, $C_1$–$C_4$-alkylthio or substituted or unsubstituted phenylthio and R³ and R⁴ are identical or different and each is independently of the other hydrogen, hydroxyl, $C_1$–$C_4$-alkoxy, substituted or unsubstituted phenoxy, $C_1$–$C_4$-alkylthio or substituted or unsubstituted phenylthio, by reacting a benzoic acid of the formula II

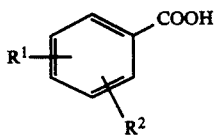

(II)

where R¹ and R² are each as defined above, with an aromatic from the benzene series which conforms to formula III

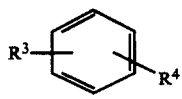

(III)

where R³ and R⁴ are each as defined above, in the presence of boron trifluoride as a catalyst in nitrobenzene as reaction medium.

2. A process as claimed in claim 1, wherein the reaction is carried out at from 20° to 200° C.

3. A process as claimed in claim 1, wherein from 1 to 3 moles of boron trifluoride are used per mole of benzoic acid of the formula II.

4. A process as claimed in claim 1, wherein said substituted phenyl is phenyl substituted by $C_{1-4}$ alkyl, $C_{1-4}$ alkoxy, hydroxyl, halogen or carboxyl.

5. A process as claimed in claim 1, wherein R¹, R², R³ and R⁴ are each independently ethoxy, propoxy, isopropoxy, butoxy, isobutoxy, sec-butoxy or tert-butoxy.

6. A process as claimed in claim 1, wherein R¹ and R² are each independently methyl, ethyl, propyl, isopropyl, butyl, isobutyl, sec-butyl, tert-butyl, phenyl, 2- or 4-hydroxyphenyl, 2-methylphenyl, fluorine, chlorine, bromine, 4-carboxyphenoxy, 4-chlorophenoxy, methylthio, ethylthio, propylthio, isopropylthio, butylthio or 4-methylphenylthio.

7. A process as claimed in claim 1, wherein said benzoic acid of FOrmula II is one member selected from the group consisting of benzoic acid, 2-hydroxybenzoic acid, 3-hydroxybenzoic acid, 4-hydroxybenzoic acid, 2,4-dihydroxybenzoic acid, 3,5-dihydroxybenzoic acid, 2-methoxybenzoic acid, 3-methoxybenzoic acid, 4-methoxybenzoic acid, 2-fluorobenzoic acid, 3-fluorobenzoic acid, 4-fluorobenzoic acid, 2-chlorobenzoic acid, 3-chlorobenzoic acid, 4-chlorobenzoic acid, 2-bromobenzoic acid, 3-bromobenzoic acid, 4-bromobenzoic acid, 2-methylbenzoic acid, 3-methylbenzoic acid, 4-methylbenzoic acid, 2-phenylbenzoic acid, 3-phenylbenzoic acid, 4-phenylbenzoic acid, 4-hydroxybiphenyl-4'-carboxylic acid, 2,4-dimethoxybenzoic acid, 2,6-dimethoxybenzoic acid, 4-carboxydiphenyl ether and 4,4'-dicarboxydiphenyl ether.

8. A process as claimed in claim 1, wherein said aromatic of Formula III is one member selected from the group consisting of benzene, phenol, phloroglucine, resorcinol, hydroquinone, anisole, resorcinol dimethyl ether, hydroquinone dimethyl ether and hydroquinone methyl ether.

9. A process as claimed in claim 1, comprising injecting boron trifluoride gas, with stirring, into a mixture of said benzoic acid or Formula II in said aromatic of Formula III in nitrobenzene.

10. A process as claimed in claim 1, wherein the reaction is carried out at from 20° to 130° C.

11. A process as claimed in claim 1, wherein the reaction is carried out at from 50° to 90° C.

12. A process as claimed in claim 1, wherein the reaction is carried out for 0.5 to 5 hours.

13. A process as claimed in claim 1, wherein a molar ratio of said benzoic acid of Formula II and said aromatic of Formula III of from 1:0.5 to 1:2 is used.

* * * * *